US009129044B2

(12) United States Patent
Shih et al.

(10) Patent No.: US 9,129,044 B2
(45) Date of Patent: Sep. 8, 2015

(54) SYSTEM AND METHOD FOR RADIATION DOSE REPORTING

(75) Inventors: George Shih, New York, NY (US); Devin Kennedy, Boston, MA (US); Ramin Zabih, Ithaca, NY (US); Edward L. Nickoloff, Orangeburg, NY (US); Zheng Feng Lu, Emerson, NJ (US)

(73) Assignees: Cornell University, Ithaca, NY (US); The Trustees of Columbia University in the City of New York, New York, NY (US)

( * ) Notice: Subject to any disclaimer, the term of this patent is extended or adjusted under 35 U.S.C. 154(b) by 96 days.

(21) Appl. No.: 13/098,228

(22) Filed: Apr. 29, 2011
(Under 37 CFR 1.47)

(65) Prior Publication Data

US 2012/0106817 A1    May 3, 2012

Related U.S. Application Data

(60) Provisional application No. 61/329,840, filed on Apr. 30, 2010.

(51) Int. Cl.
| | |
|---|---|
| *G06K 9/00* | (2006.01) |
| *G06F 19/00* | (2011.01) |
| *A61B 6/03* | (2006.01) |
| *A61B 6/00* | (2006.01) |

(52) U.S. Cl.
CPC .............. *G06F 19/321* (2013.01); *A61B 6/583* (2013.01); *A61B 6/032* (2013.01); *A61B 6/542* (2013.01); *A61B 6/563* (2013.01)

(58) Field of Classification Search
USPC .................................................. 382/131, 128
See application file for complete search history.

(56) References Cited

U.S. PATENT DOCUMENTS

| | | | |
|---|---|---|---|
| 5,661,773 A | 8/1997 | Swerdloff et al. | |
| 6,744,846 B2 | 6/2004 | Popescu et al. | |
| 6,870,549 B1 | 3/2005 | Swann et al. | |
| 7,627,079 B2 | 12/2009 | Boone | |
| 2001/0048027 A1* | 12/2001 | Walsh | 235/385 |
| 2004/0131141 A1 | 7/2004 | Horiuchi | |
| 2005/0165294 A1 | 7/2005 | Weiss | |
| 2006/0018435 A1 | 1/2006 | Toth et al. | |
| 2006/0111943 A1 | 5/2006 | Wu | |
| 2006/0259282 A1 | 11/2006 | Failla et al. | |
| 2007/0116183 A1 | 5/2007 | Ueki et al. | |
| 2008/0103834 A1* | 5/2008 | Reiner | 705/3 |
| 2009/0024053 A1* | 1/2009 | Kasahara | 600/547 |
| 2009/0192813 A1* | 7/2009 | Gejdos et al. | 705/1 |
| 2009/0226060 A1* | 9/2009 | Gering et al. | 382/128 |
| 2010/0042434 A1 | 2/2010 | Luo et al. | |

(Continued)

OTHER PUBLICATIONS

International Search Report and Written Opinion for PCT/US2011/034624, mailed Jul. 28, 2011.

(Continued)

*Primary Examiner* — Matthew Bella
*Assistant Examiner* — Weiwen Yang
(74) *Attorney, Agent, or Firm* — Foley & Lardner LLP

(57) ABSTRACT

Systems and method can be employed to automatically extract radiation dose information from medical images, particularly a plurality of heterogeneous CT images including those from legacy CT scanners. A report including the extracted radiation dose information can be generated, and alerts can be sent to reduce the possibility of overexposures.

49 Claims, 8 Drawing Sheets

(56) References Cited

U.S. PATENT DOCUMENTS

2010/0091950 A1    4/2010    Ellinwood et al.
2011/0129057 A1*    6/2011    Paul et al. .......................... 378/4

OTHER PUBLICATIONS

Müller, et al., "Automated Object extraction for Medical Image Retrieval Using the Insight Toolkit (ITK)." Third Asia Information Retrieval Symposium, AIRS 2006, Singapore, Oct. 16-18, 2006, 14 pages.

Kennedy, et al., "Automated detection and Supervised Removal of Protected Health Information embedded in DICOM Images: Development of technology and User-Interface Incorporated into research Workflow." 2009 RSNA Annual Meeting, Nov. 29-Dec. 4, 2009, 2 pages.

J.R. Mayo, "Radiation dose issues in longitudinal studies involving computed tomography." Proc Am Thorac Soc 2008; 5, pp. 934-939.

European Guidelines on Quality Criteria for Computed Tomography, EUR 16262 EN (1999). Web site print Jul. 20, 2011, 2 pp.

Thomas, et al., Age-specific effective dose for pediatric MSCT examinations at a large children's hospital using DLP conversion coefficients: a simple estimation method, Pediatr Radiol 2008; 38:645-656.

Lu, et al., Pediatric Patient Dose Management From a 64 Slice VCT, Med. Phys. 2007; 34(6), p. 2339-2340.

Neumann, et al., "Tracking Radiation Exposure From Diagnostic Imaging Devices." NIH, 2010, vol. 7, Issue 2, pp. 1-4.

C. Masters, "Should you have a CT scan?" Time, Jul. 17, 2007. Web site print Jul. 20, 2011, 2 pp.

R.C. Rabin, "With Rise in Radiation Exposure, Experts Urge Caution on Tests." The New York Times, 2007, Web site print Jul. 20, 2011, 3 pp.

A. Mozes, "Certain Tests in ERs Raise Cancer Risk for Some." The Washington Post, 2008, Web site print Jul. 20, 2011, 2 pp.

Einstein, et al., "Estimating Risk of Cancer Associated with Radiation Exposure from 64-Slice Computed Tomography Coronary Angiography." JAMA, 2007, vol. 298:3, pp. 317-323.

Kim et al., "Coronary artery calcification screening: estimated radiation dose and cancer risk." Arch Intern Med, 2009; 169 (13): 1188-1194, pp. 1-12.

Pierce, et al., "Radiation-Related Cancer Risks at Low Doses among Atomic Bomb Survivors." Radiation Research 154; 2000, pp. 178-186.

"Health Risks from Exposure to Low Levels of Ionizing Radiation." BEIR VII—Phase 2, Washington, DC: National Academy of Sciences; 2006, 423 pages.

R. Mezrich, "Are CT Scans Carcinogenic?" Journal of American College of Radiology, 2008, pp. 691-693.

I.N. Daher, "Radiation Doses Associated with Cardiac Computed Tomography Angiography." JAMA. 2009; Vo. 301, No. 22, p. 2324.

Hall, et al., "Radiobiology for the Radiologist." 6th ed.. New York: Lippincott, Williams & Wilkins; 2005, 3 pp.

"Recommendations of the International Commission on Radiological Protection." Annals of the ICRP, 1977; :1-47, 49-53.

Tao, et al, Cancer Mortality in the High Background Radiation areas of Yangjiang, China during the period between 1979 and 1995. J. Radiat. Res. 41, 2000; pp. 31-41.

Nair, et al, Background Radiation and Cancer Incidence in Kerala, India—Karanagappally Cohort Study. Health Physics Society, 2009; vol. 96, 12 pp.

D.A. Schauer, et al. "NCRP Report No. 160, ionizing radiation exposure of the population of the United States, medical exposure—are we doing less with more, and is there a role for health physicists?". Health Physics Society 2009, vol. 97, pp. 1-5.

Amis, et al., "American College of Radiology White Paper on Radiation Dose in Medicine." Journal of the American College Radiology, vol. 4., 2007; pp. 272-284.

"American College of Radiology, Radiological Society of North America. Safety: radiation exposure in x-ray examinations," Mar. 2007, 4 pp. http://www.radiologyinfo.org/content/safety/xray_safety.htm Accessed Jun. 10, 2009, Printed Jul. 20, 2011, 5 pp.

W. Bogdanich, "Radiation Overdoses Point Up Dangers of CT Scans", Oct. 16, 2009, http://nytimes.com/2009/10/16/us/16radiation. Accessed on Apr. 25, 2010, Printed Jul. 20, 2011, 3 pp.

Image Gently: "The Alliance for Radiation Safety in Pediatric Imaging", http://www.pedrad.org/associations/5364/ig/imagegently. Accessed on Apr. 25, 2010. Printed Jul. 20, 2011, 6 pp.

Singh, et al., "Dose Reduction and Compliance with Pediatric CT Protocols Adapted to Patient Size, Clinical Indication, and Number of Prior Studies." Radiology, vol. 252: No. 1; Jul. 2009, pp. 200-206.

National Council on Radiation Protection and Measurements, Report No. 160, "Ionizing Radiation Exposure of the Population of the United States", Bethesda, MD, 2009.

Berrington De González, et al. " Projected Cancer Risks from Computed Tomographic Scans Performed in the United States in 2007." Arch Intern Med. 2009;169(22), pp. 2071-2077.

"Health risks from exposure to low levels of ionizing radiation: BEIR VII Phase 2 Report" (Committee to Assess Health Risks from Exposure to Low Levels of Ionizing Radiation, National Research Council). Washington DC: National Academy Press, 2006, 423 pp.

G. Harris, "Scientists Say F.D.A. Ignored Radiation Warnings", Mar. 28, 2010, http://www.nytimes.com/2010/03/29/health/policy/29fda.html. Accessed on Apr. 25, 2010, Printed Jul. 21, 2011, 3pp.

Brenner, et al., "Computed Tomography—An Increasing Source of Radiation Exposure." The New England Journal of Medicine; 2007;357, pp. 2277-2284.

Preston, et al., "Studies of Mortality of Atomic Bomb Survivors. Report 13: Solid Cancer and Noncancer Disease Mortality: 1950-1997." Radiation Research Society 2003; vol. 160, pp. 381-407.

B. Mason, "Pocket-Sized Workout Pal Is Data Geek's Dream", Oct. 16, 2009, http://www.wired.com/reviews/product/pr_fitbit. Accessed on Apr. 25, 2010, Printed Jul. 20, 2011, 6pp.

N. Anderson, "Firm uses typing cadence to finger unauthorized users", http://arstechnica.com/tech-policy/news/2010/02/firm-uses-typing-cadence-to-finger-unauthorized-users.ars. Accessed on Apr. 25, 2010, Printed Jul. 20, 2011, 2pp.

Casey, et al.,. "A survey of methods and strategies in character segmentation." IEEE Transactions on Pattern Analysis and Machine Intelligence, 1996;18(7) 31pp.

Ogden, et al., "Patient Size and X-Ray Transmission in Body CT." Health Physics, 2004; vol. 86, No. 4, pp. 397-405.

Huda, et al., "Radiation doses to infants and adults undergoing head CT examinations." Medical Physics. vol. 28, No. 3, Mar. 2001; pp. 393-399.

Nickoloff, et al., "Influence of Phantom Diameter, kVp and Scan Mode Upon Computed Tomography Dose Index." Medical Physics 2003: vol. 30, No. 3, pp. 395-402.

Nickoloff, et al., "Comparison of Radiation Dose Indexes for CT Scanners: Measured Versus Automated Scanner Calculations." Presentation at the 47th Annual Meeting of AAPM, Seattle, WA, Med. Phys. 2005; 32(6), p. 1906.

Nickoloff, et al., "Radiation Dose Descriptors: BERT, COD, DAP, and Other Strange Creatures." Radiographics Sep.-Oct. 2008; vol. 28, No. 5, pp. 1439-1451.

Nickoloff, et al.,, Direct Measurement of Pediatric CT Dose and Comparison to CTDI Data, presentation at the IOMP's 14th International Conference of Medical Physics, Nuremberg, Germany, Sep. 14-17, 2005, 2 pages.

* cited by examiner

FIG. 1

SYSTEM AND METHOD FOR RADIATION DOSE REPORTING

CROSS-REFERENCE TO RELATED APPLICATION

The present application claims priority to U.S. Provisional Patent Application No. 61/329,840 filed Apr. 30, 2010, the disclosure of which is hereby incorporated by reference in its entirety.

FIELD

The present disclosure is directed to systems and methods for reporting radiation dose information from medical images, particularly the radiation doses from Computed Tomography (CT) image dose screens.

BACKGROUND

Approximately 70 million CT studies are performed each year in the U.S., which accounts for about 50% of the radiation dose exposure administered in the healthcare setting. In large part due to CT scans, the average lifetime diagnostic radiation dose received by patients is up sevenfold from 1980. Numerous studies and reports have been published recently concerning potential dangers of low-dose radiation exposure (similar to the dose levels from 2-3 CT studies). A standard CT scan of the abdomen/pelvis is equivalent to approximately 150-200 chest X-rays. Thus, for a patient who has had a CT scan and a number of X-rays, the larger contribution to the radiation dose exposure likely results from the CT scan (although there are other procedures such as the PET-CT, and long interventional procedures using fluoroscopy, which also contribute to significant radiation exposures). Pediatric patients are at higher risks compared to adults for a given radiation dose.

Adverse events involving inadvertent healthcare-related radiation overexposure involving CT have caused much public concern about the safety of CT scans. In one instance, a hospital gave 8× the normal dose for head CT studies involving more than 250 patients. In another instance, a two-year old pediatric patient had the same region of his head scanned over 150 times, lasting over an hour during the CT exam. These radiation overexposure events can occur because of policy errors (e.g., flawed CT protocols), human errors, or machine errors. Physicians can attempt to minimize the possibility of these risks, and correct the errors before they cause detrimental effects to patients, but only to the extent that these radiation overexposure events can be detected.

Some of the overexposures were only detected as a result of patient symptoms (e.g., erythema, hair loss, etc) or observations by the patients or their family members. Recent campaigns promoting radiation safety and awareness such as "Image Gently," and the color coding of pediatric low-dose protocols by vendors to increase compliance, have improved awareness for both the public and medical professionals. However, these efforts may not be sufficient.

In addition to diagnostic CT, use of CT for screening studies has also dramatically increased, particularly for lung and colon cancers. There have been concerns about the risk of radiation exposure from CT colonography.

The increase in CT usage partly results from demand increase from both referring clinicians and patients themselves. Improvements in CT scanners in image quality and functionality make these studies easier to perform, and this may also increase the tendency of more CT studies.

While there are no studies yet directly connecting CT radiation to cancer-related deaths, some recent studies have attempted to extrapolate the risk of CT-associated cancers to the data from the Hiroshima atomic bomb survivors. One particular atomic bomb survivor cohort of 25,000 people received an average dose of 40 millisieverts (mSV) (roughly the equivalent of 2-3 CT studies) demonstrated a significant increase in overall cancer risk and mortality. One commonly cited publication estimates that up to 1.5-2% of all current cancers in the U.S. may be attributed to CT studies, and therefore despite of a small individual risk, the population risk to CT use may be significant.

SUMMARY

In one aspect, a method is provided including automatically extracting radiation dose information from medical images, and generating a report including the extracted radiation dose information.

In one embodiment, the medical images include one of computed tomography (CT) or positron emission tomography-computed tomography (PET-CT) images.

In one embodiment, the automatically extracting dose information includes performing an image segmentation on the medical images. The performing an image segmentation can include performing a connected component analysis. The connected component analysis can be performed using DCMTK.

In one embodiment, the method further includes an optical character recognition (OCR) process to convert the segmented images from binary data into textual data.

The method can further include correcting a patient size. The correcting can include obtaining a relationship between patent size and weight. In one embodiment, the correcting further includes calculating an equivalent cylindrical phantom diameter. The calculating can include calculating the equivalent cylindrical phantom diameter using: phantom diameter=square root (AP dimension*LAT dimension)*C, wherein C is the correction factor that takes into consideration of the density difference in soft tissue and in acrylic PMMA phantom material, AP dimension is a patient's anteriorposterior dimension, and LAT dimension is the patient's lateral dimension. The method can further include generating a correction factor as a function of patient weight for each CT scanner.

In one embodiment, the method further includes determining a body portion of the patient that is scanned, wherein said correcting a patient size comprises correcting the patient size using a formula specific to the body portion.

In one embodiment, the extracted radiation dose information comprises an effective dose.

The method can further include storing the dose information in a database.

In one embodiment, the method further includes storing the dose information in DICOM metadata of a medical image.

In one embodiment, the automatically extracting dose information includes extracting dose information from medical images obtained from a plurality of heterogeneous CT scanners. In one example, at least some of the medical images obtained from some of the plurality of heterogeneous CT scanners are not in DICOM format.

In one embodiment, the method further includes comparing the extracted radiation dose information with a predetermined threshold. The method can further include providing an alert if a radiation dose from the extracted radiation dose information is higher than a predetermined threshold.

In one embodiment, the method further includes displaying the report through a web interface.

In one embodiment, the generating a report includes generating at least one of an effective dose, an accumulative dose, or an average dose for a patient. The method can further include providing an alert if a new CT study is ordered and if an accumulative dose exceeds a predetermined threshold.

In another embodiment, the generating a report comprises generating a summary of a healthcare provider's history of ordering radiation-based studies.

In one embodiment, the method further includes sending the report through one of a short message, an email, a website, or a voice message.

In another aspect, a system is provided including a computer configured to automatically extract dose information from a medical image and to generate a dose information report.

In one embodiment, the system includes a plurality of heterogeneous scanners, wherein at least some of the scanners are configured to output image data not in DICOM format. The medical image can include one of computed tomography (CT) or positron emission tomography-computed tomography (PET-CT) images, for examples.

In one embodiment, the system further includes a communication device configured to transmit the dose information report to a user.

In one embodiment, the system further includes at least one of a picture archiving and communication system (PACS) or a radiology information system (RIS).

In another aspect, a non-transitory computer readable medium is provided containing instructions therein, wherein the instructions include automatically extracting dose information from a medical image, and generating a dose information report.

In one embodiment, the medical images include one of computed tomography (CT) or positron emission tomography-computed tomography (PET-CT) images.

In one embodiment, the automatically extracting dose information includes performing an image segmentation on the medical images, which includes, for example, performing a connected component analysis. The connected component analysis can be performed using DCMTK.

In one embodiment, the instructions further include converting the segmented images from binary data into textual using optical character recognition (OCR).

In one embodiment, the instructions further include correcting a patient size. The correcting can include obtaining a relationship between patent sizes and weights, and can further include calculating an equivalent cylindrical phantom diameter. The calculating can include, for example, calculating the equivalent cylindrical phantom diameter using: phantom diameter=square root (AP dimension*LAT dimension)*C, wherein C is the correction factor that takes into consideration of the density difference in soft tissue and in acrylic PMMA phantom material, AP dimension is a patient's anterior posterior dimension, and LAT dimension is the patient's lateral dimension. In one embodiment, the instructions further include generating a correction factor as a function of patient weight for a CT scanner.

In one embodiment, the instructions further include storing the dose information in a database.

In one embodiment, the instructions further include storing the dose information in DICOM metadata of a medical image.

In one embodiment, the automatically extracting dose information includes extracting dose information from a plurality of heterogeneous CT scanners.

In one embodiment, at least some of the dose information extracted from at least some of the plurality of heterogeneous CT scanners are not in DICOM format.

In one embodiment, the instructions further include comparing the extracted radiation dose information with a predetermined threshold. In one example, the instructions further include providing an alert if a radiation dose from the extracted radiation dose information is higher than a predetermined threshold.

In one embodiment, the instructions further include displaying the dose information report through a web interface.

The generating a report can include generating an accumulative or an average radiation dose information for a patient.

The instructions can further include providing an alert if a new CT study is ordered and if an accumulative dose exceeds a predetermined threshold.

In another embodiment, the generating a report includes generating a summary of a healthcare provider's history of ordering radiation-based studies.

The instructions can further include sending the report through one of a short message, an email, a website, or a voice message.

BRIEF DESCRIPTION OF THE DRAWINGS

FIG. 1 is an image header of a CT dose screen from a legacy CT scanner showing dose information in accordance with an illustrative embodiment.

DETAILED DESCRIPTION

Figure 2:
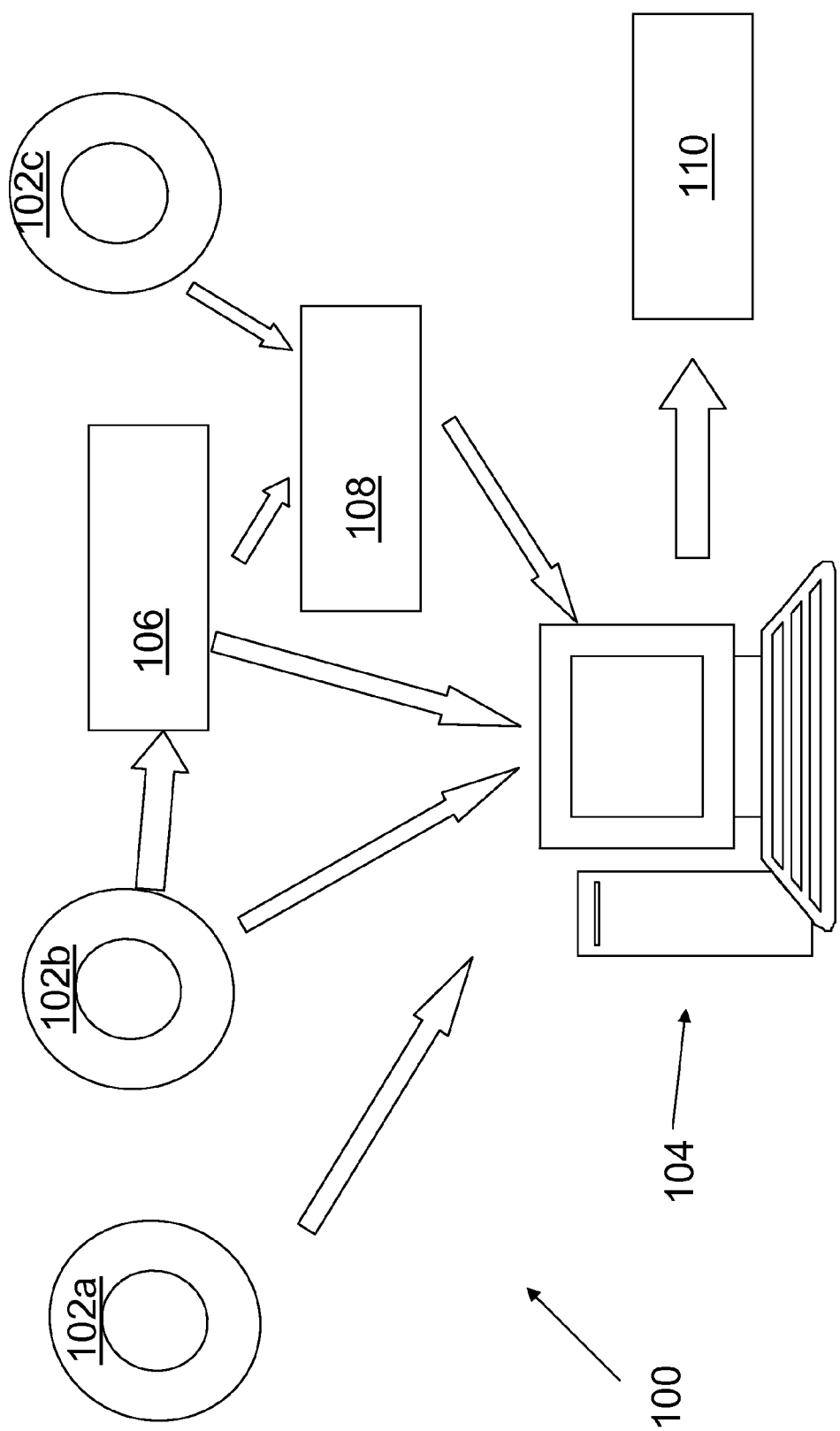
FIG. 2 is a schematic diagram illustrating a system for automatically extracting radiation dose information from medical images according to one representative embodiment.

In the following description, reference is made to the accompanying drawings that illustrate some specific embodiments which may be practiced. These embodiments are described in detail to enable those skilled in the art to practice the embodiments disclosed herein, and it is to be understood that other embodiments may be utilized and that structural, logical and electrical changes may be made without departing from the scope of the attached claims. The contents of any cited references (including literature references, issued patents, published patent applications as cited throughout this application) are hereby expressly incorporated by reference.

As described above, the potential dangers of healthcare-related radiation dose exposures need to be taken into account when CT studies are prescribed. To quantify such dangers, the radiation dose should be quantified accurately.

Absorbed dose is the measure of the radiation energy absorbed in a tissue. The unit is gray (Gy), or one joule of energy absorbed per kilogram of tissue. However, it is difficult to measure this quantity in tissue as it is difficult to place radiation dosimeters inside tissues or organs. Thus, the absorbed dose in tissues is typically obtained indirectly. For example, absorbed dose can be measured inside a "phantom," i.e., a block of plastic, polymethylmethacrylate (Plexiglas, or PPMA), or water. The phantom often has a cylindrical form. Dosimeters can be inserted inside the phantom, which is exposed to calibrated radiations in the CT scanner. The measured dose values in the phantom can then be used to estimate the dose values in the patient's tissues. As a result, radiation dose received by a patient as reported from CT scanners is actually the dose received by a cylindrical phantom.

A conventionally used CT radiation dose parameter is the CT dose index (CTDI), which can be measured using dosimeters. CTDI is typically measured in units of Gy, or milligrays (mGy), and is an indication of dose concentration. Image noise in the CT images can be reduced with an increase in the X-ray intensity, and/or the exposure time. The X-ray intensity increases with the X-ray tube voltage, which is expressed in peak kilovolts (kVp), typically in the 100 kVp range. The product of the tube current multiplied by the exposure time, expressed in milliampere seconds (mAs, typically in the 100 mAs range), is usually proportional to the radiation dose.

The biological impact of the radiation, such as the risk of cancer, is often related to the types of radiation and the integral dose. Dose Equivalent, in unit of Sv, is defined by the radiation dose multiplied by a weighting factor ($W_R$) that characterizes the type of radiation. For example, for CT imaging, $W_R=1$. For proton beams used for radiation therapy, $W_R>1$.

Figure 1:
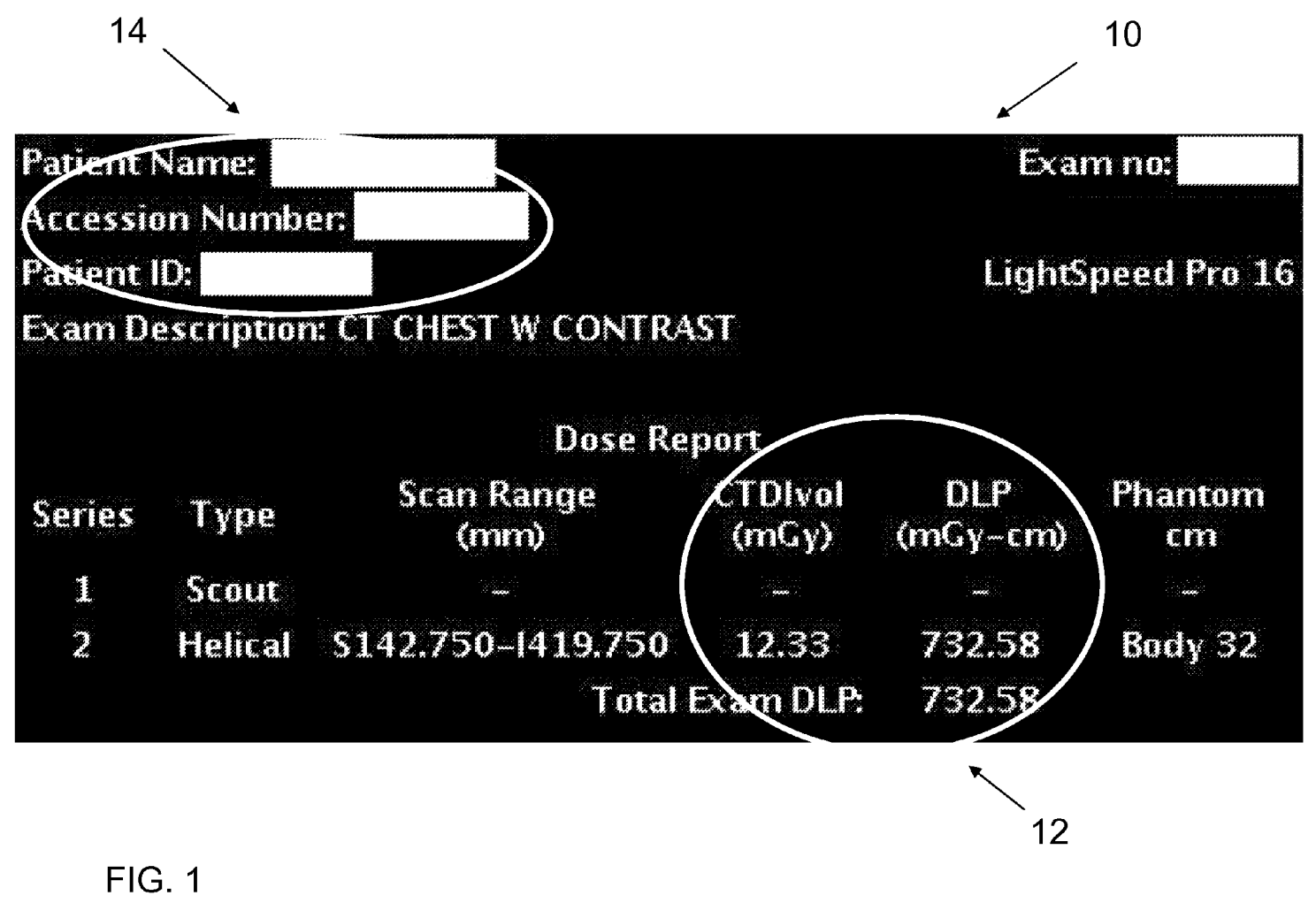

The volume CTDI (CTDIvol) is often reported in the image headers, or "dose screens," of legacy CT scanners, as illustrated in FIG. 1. CTDIvol describes the average dose delivered to the scan volume for a study. Another parameter often included in the dose screen is the dose-length product (DLP, the product of CTDIvol and the scan length), which is an indicator of the integrated radiation dose of an entire CT examination. DLP is generally proportional to CTDI.

Effective dose, also in units of Gy, takes into account that different parts and organs of the body have different sensitivities to the radiation, and is defined as the absorbed dose multiplied by a weighting factor $W_T$. The weighting factor $W_T$ is typically normalized to 1 for the total body, and is about 0.12 for the lung, and 0.03 for thyroid.

The inventors have recognized the potential dangers of healthcare-related radiation dose exposures. Embodiments disclosed herein provide radiation dose exposure monitoring and tracking to reduce the risks associated with these radiation dose exposures. In one embodiment, systems and methods are provided for automatically tracking and trending CT or other radiation exposures. An automatic system is provided to detect inadvertent radiation overexposures and send out immediate alerts. The system can also provide the long-term need for health-care providers and patients to better understand the risks of low-dose radiation exposures such as those from CT studies.

In a representative embodiment, the tracking of CT dose information is completely automated. Heterogeneous CT scanners, including legacy scanners and newer scanners, and the medical images produced therefrom, can be integrated into the system without relying on future improvements from CT manufacturers. Newer CT scanners likely will adopt the Digital Imaging and Communications in Medicine (DICOM) structured reporting (SR) Dose Reporting standard, but it is unlikely that the large number of legacy CT scanners will ever be upgraded to this standard.

Integrating the Healthcare Enterprise (IHE) is currently working on standardizing new CT scanners with respect to radiation dose reporting. However, only the newest of CT scanners have the capability of generating these radiation dose reports according to the newer standards, and include radiation dose information in the DICOM metadata. As a result, the vast majority of existing CT scanners do not have the capability to work with this new IHE standard for dose reporting. Even if a CT scanner is sufficiently recent, or is upgraded to support this new standard, other information systems such as the PACS (picture archiving and communication system) and RIS (radiology information system) must also support it. It will likely be years (e.g., 10-15 years) before appropriate infrastructures in hospitals across the U.S. include machines and computer systems sufficiently upgraded to a point where radiation dose tracking can use this new IHE standard. It will likely take many more years to achieve this goal world wide.

In one embodiment, radiation dose information is extracted from CT dose screens from legacy CT scanners. FIG. 1 is an example of a CT dose screen from a legacy CT scanner showing dose information, such as the CTDIvol, the DLP, and the total DLP. The dose screen is human-readable, but not readily machine-readable.

As a result, substantial image processing is performed in accordance with representative embodiments disclosed herein to extract the radiation dose information from these legacy dose screens. In one embodiment, the extracted radiation dose information can be converted into and stored as DICOM metadata.

Embodiments disclosed herein allow hospitals, clinics, etc. to implement radiation dose tracking of existing radiation scanners without the new IHE standard. The difficulties in finding inadvertent radiation overexposure cases and other errors during radiation exams result from the lack of capability to systematically track and assess each instance of radiation exposure for a given patient. Specifically, limitations exist in the way the CT image information provided by the modality manufacturers. As a result, it is difficult to provide automated quality control and tracking for inadvertent radiation overexposures, or to share the radiation dose data with other information systems.

In one embodiment, an automated framework is provided for digital radiation dose reporting obtained from dose screens. The system can reliably extract radiation dose information from radiation dose report images, creating a completely automated process in which additional processing of this radiation dose information can be performed. Inadvertent radiation overexposures can then be automatically detected. The dose information can be sent to downstream medical information systems to provide better feedback for the education of physicians, patients, and the general public.

In one representative embodiment, with reference to FIG. 2, a system 100 is provided to realize the automatic dose information extraction, analysis, and transmission. The system 100 can include a plurality of apparatuses 102a, 102b, and 102c configured to generate medical images that include some form of dose information. In alternative embodiments, additional or fewer apparatuses for generating medical images may be included in the system 100. In an illustrative embodiment, the apparatuses 102a, 102b, and 102c can be heterogeneous CT scanners. Alternatively, the apparatuses 102a, 102b, and 102c can be positron emission tomography (PET) scanners, X-ray radiography machines, fluoroscopy devices, and/or any other medical devices that generate radiation and that are capable of generating medical images. The apparatuses 102a, 102b, and 102c can be located within a single hospital or other medical institution, or across a plurality of distinct medical institutions.

In an illustrative embodiment, the apparatuses 102a, 102b, and 102c are configured to generate medical images based on patient scans as known to those of skill in the art.

Images obtained from newer CT scanners may already include radiation dose information stored as DICOM metadata. As a result, radiation dose information can be obtained from such images with only minimal processing of the DICOM metadata as known to those of skill in the art.

However, images generated with legacy CT scanners generally do not include radiation dose information in DICOM metadata. Rather, in such older devices, the radiation dose information (or information that can be used to determine the radiation dose) is embedded in the medical image in the form of a dose screen as illustrated in FIG. 2.

In one embodiment, the medical images generated by the apparatuses 102a, 102b, and 102c can be directly transmitted to a server or computer 104 for image processing and conversion. The computer 104 can be implemented as a desktop computer, a laptop computer, a portable communications device, or any other type of computing device. Alternatively, the generated medical images may be transmitted to an image conversion device 106 for processing and conversion, and transferred from the image conversion device 106 to the computer 104 for storage and/or further processing. The generated medical images may also be transmitted to a database (or other computer memory) 108 for storage. In an alternative embodiment, the database 108 may be incorporated into the computer 104 and/or the image conversion device 106. The memory device(s) included in the system 100 may be of any type including, but not limited to, volatile memory (such as RAM), non-volatile memory (such as ROM, flash memory, etc.) or any combination thereof. Examples of removable storage and non-removable storage devices that may be included in the system 100 include magnetic disk devices such as flexible disk drives and hard-disk drives (HDD), optical disk drives such as compact disk (CD) drives or digital versatile disk (DVD) drives, solid state drives (SSD), tape drives, etc. Example computer storage media may include volatile media, nonvolatile media, removable media, non-removable media, etc. implemented in any method or technology for storage of information, such as computer readable instructions, data structures, program modules, etc.

Communication between the elements of the system 100 can be implemented using any form of wired or wireless communication as known to those of skill in the art. In one embodiment, a bus/interface controller may be used to facilitate communications between the apparatuses 102a, 102b, and 102c, the computer 104, the image conversion device 106, and the database 108.

In an illustrative embodiment, the computer 104 and/or the image conversion device 106 perform image processing on received medical images to automatically extract radiation dose information from the dose screens of the medical images. The computer 104 and/or image conversion device 106 can include, for example, an application-specific integrated circuit (ASIC) chip or a processor configured to extract the radiation dose information from the medical images. The processor(s) used in the system 100 may be of any type including, but not limited to, a microprocessor, a microcontroller, a digital signal processor (DSP), or any combination thereof.

The image processing can include, for example, a connected component analysis in which subsets of connected components of a digital image are grouped/labeled based on one or more given heuristics as known to those of skill in the art. Any form of a connected component analysis, or any other image processing methods generally known to those of skill in the art, may be used.

In one embodiment, the connected component analysis can be performed using a DICOM ToolKit (DCMTK). In an alternative embodiment, any other type of image labeling or segmentation algorithm known to those of skill in the art may be used.

The results from the image segmentation analysis may be binary data. The binary data can be further processed using an optical character recognition program (OCR) or other recognition program to convert the binary data into text, which can be stored and manipulated in subsequent downstream applications. The image conversion device 106 can include OCR software and/or hardware. Any type of OCR process known to those of skill in the art may be used. In a representative embodiment, the OCR operation can be performed using a modified version of the open-source OCR called Tesseract (Apache 2.0 License).

In an alternative embodiment, other recognition algorithms such as intelligent character recognition (ICR), etc. may be used.

The radiation dose information processed by the computer 104 and/or the image conversion device 106 can be presented and/or stored in the form of a summary, a report, a notification, or an alert, and can be sent to a healthcare professional 110 via a text message, an email, a website, a voice message, etc. In one embodiment, a communication device can be employed to realize the communications among the different devices and to transmit the report and/or alert to the healthcare provider 110. The communication device can include a network controller, which may be arranged to facilitate communications with one or more other computing devices over a network communication link via one or more communication ports. In one embodiment, the system 100 may a include small-form factor portable (or mobile) electronic device such as a cell phone, a personal data assistant (PDA), a personal media player device, a wireless web-watch device, a personal headset device, an application specific device, etc. for receiving/transmitting patient records, medical images, radiation dose data, etc.

Figure 3:
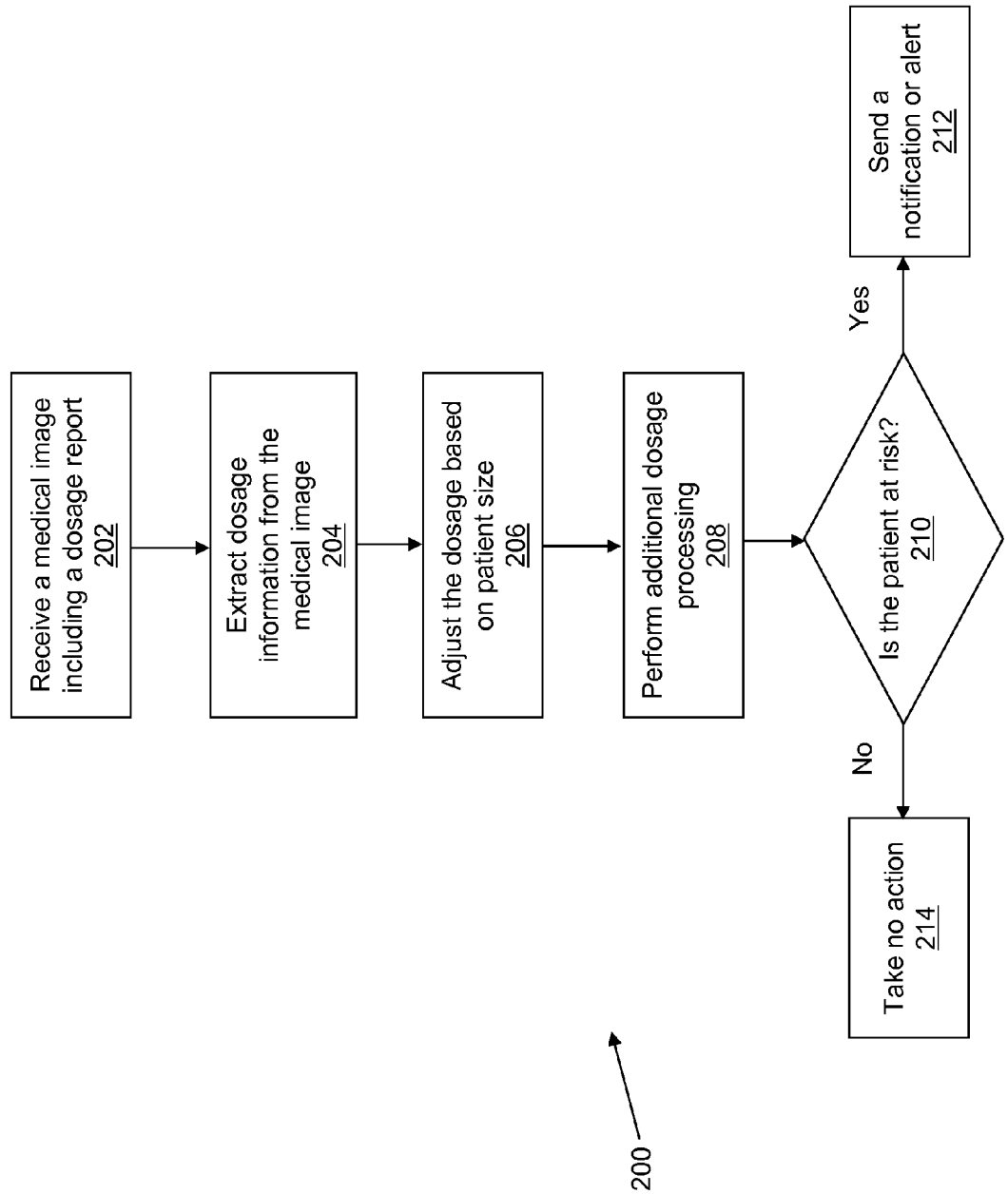
FIG. 3 is a flowchart illustrating a method for automatically extracting radiation dose information from medical images according to one representative embodiment.

FIG. 3 is a flow diagram illustrating an automated workflow 200 in accordance with an illustrative embodiment. In alternative embodiments, additional, fewer, and/or different operations may be performed. Also, the use of a flow diagram is not meant to be limiting with respect to the order of operations performed. In one embodiment, a medical image including a dose report or radiation dose information (e.g., in the form of a dose screen) can be automatically generated by a scanner each time that a patient is scanned. The scanner may be any X-ray emitting scanner, including an X-ray machine, a CT scanner, a PET-CT scanner, fluoroscopy equipment, etc. In an illustrative embodiment, the medical image includes at least an identification of the patient that was scanned. The patient identification can be a name, an identification number, or any other information that can be used to link the dose report to the patient, such as those illustrated in FIG. 1.

In an operation 202, a medical image including a dose report (or other radiation dose information) is received by the system. With reference to FIG. 1, the medical image may be received by the computer 104 and/or the image conversion device 106. The dose report can be sent via a standard DICOM "send" or by any other method, depending on the embodiment. An automated DICOM "send" may be communication protocol-specific, and may involve a one-time manual adjustment for each communication protocol to be used. In addition to standard patient information (e.g., name, age, gender, etc.), patient weight, height, body measurements, etc. can also be sent to the system from the electronic health record (EHR) system or other source. In one embodiment, the system may request the patient information from the EHR system in response to receiving a medical image associated with the patient. In an alternative embodiment, the patient information may be incorporated into the medical image by the medical scanning device.

In an operation 204, the dose information is extracted from the medical image, for example, using computer and image processing algorithms. For example, text, symbols, and other information can be extracted from the medical images through image segmentation or labeling. Such image segmentation/labeling can be performed, for example, with a connected component analysis (connected component labeling). Thus, information in a binary image can be segmented into connected groups of identically labeled pixels which are labeled as distinct objects. In a representative embodiment, this operation can make use of an open source DICOM toolkit to perform the connected component analysis.

In an operation 206, the extracted dose can be adjusted based on the patient's size, as describe in detail below. In an operation 208, the dose information can be further processed. This additional processing may include, for example, formatting the dose information as a report. The report can include, for example, an effective dose for the patient, an average dose for the patient, a lifetime accumulative dose for the patient, etc. The dose information can be stored in a database as raw information associated with the patient, as DICOM metadata associated with the patient and/or the medical image, or in any other format. In a representative embodiment, the system may have a web-based interface, and the report generated in the operation 206 may be in the form of a web page.

The generated report can be stored in a storage device such as a memory device. In one embodiment, only the extracted dose information, e.g., the textual data extracted from the dose screen such as that illustrated in FIG. 1, is stored. In another embodiment, only the calculated effective dose, corrected for patient size is stored. In another embodiment, both the extracted dose information and the calculated effective dose are stored. In some embodiments, the factors used to calculate the effective dose, such as $W_T$, are stored. The radiation dose for each irradiation event, as well as the accumulative dose, can be stored.

The extracted dose information can be stored in a standard format, such as that recommended by IHE in its Radiation Exposure Monitoring Profile, which is based on the DICOM SR templates. The standardized format helps a large amount of extracted dose information, from heterogeneous sources, to be uniformly stored and analyzed. The sources can include, for example, CT, angiography, fluoroscopy, mammography, computed radiography (CR), digital radiography (DR), regular X-ray, radiotherapy, PET, or single-photon emission computerized tomography (SPECT). The heterogeneous data can thus be processed, analyzed, and displayed just like other DICOM data such as digital measurements or images.

The standardized format of the heterogeneous data also helps creating a national registry of the radiation exposures the patients received, as well as the statistics of the prescribing physicians.

In an operation 210, the system determines whether the patient is at risk. The patient can be at risk if an overexposure has occurred, if there is high risk for an overexposure to occur if subsequent scanning is performed on the patient, etc. These determinations can be made based at least in part on permissible radiation dose levels as known to those of skill in the art. If the patient is at risk, the system can send a notification or alert in an operation 212. The notification or alert can be sent to a physician associated with the patient that is at risk. Alternatively, the notification or alert can be sent to the patient, to a centralized radiation monitoring committee, etc. If the system determines that the patient is not at risk, no additional action may be taken. In an illustrative embodiment, the dose information may be stored and patient records can be updated regardless of whether the patient is at risk.

The above notification or alert is related to a patient. In some embodiments, a notification or alert can be related to a physician. For example, statistics on the physician's history of prescriptions of CT studies can be obtained. If such statistics shows that this physician prescribes CT studies that result in higher radiation doses for his or her patients compared with an average or with recommended values, the physician, the medical institution, or a centralized radiation monitoring committee, etc. can be notified.

Figure 4:
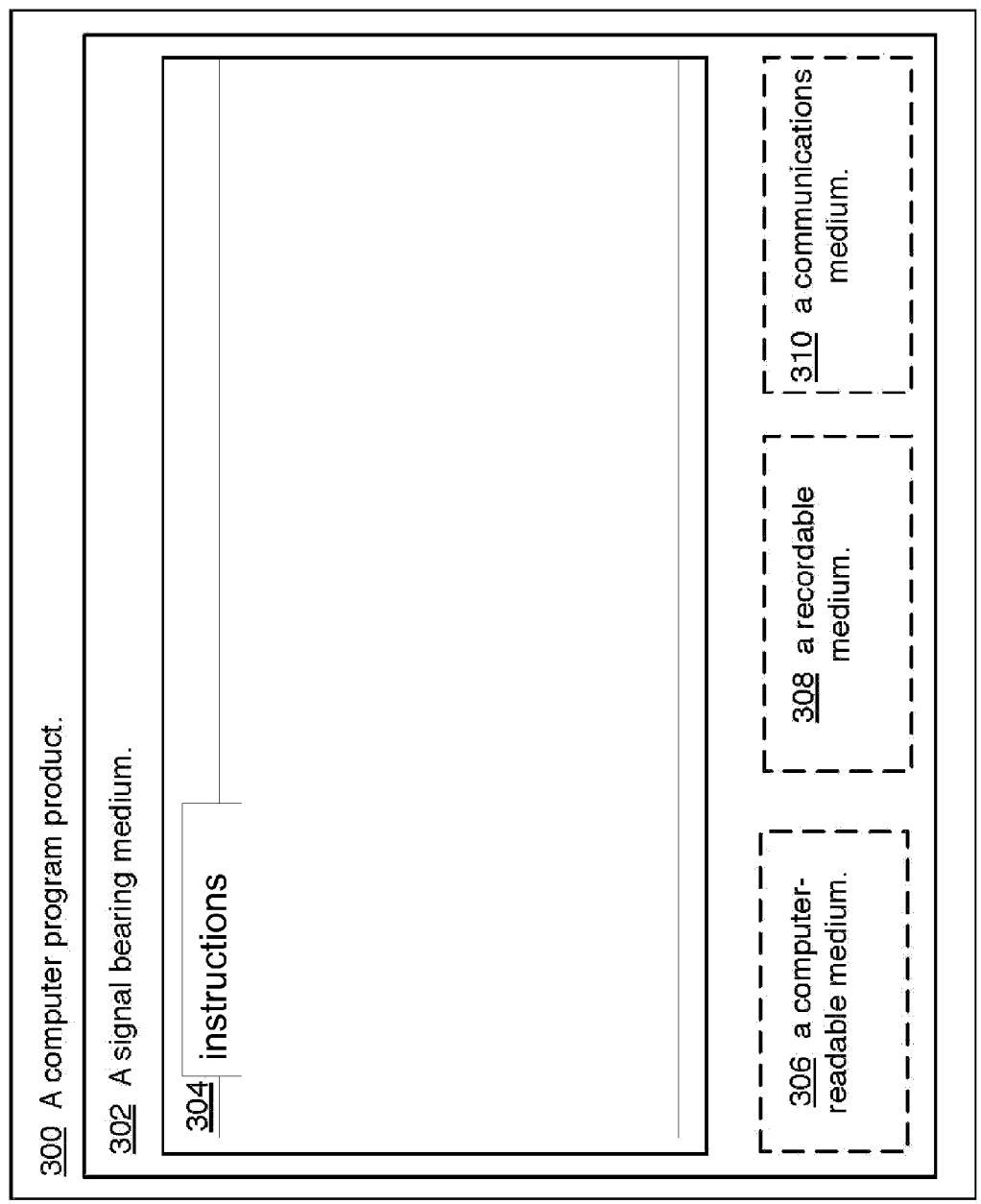
FIG. 4 is a block diagram illustrating an example computing device configured for extracting and reporting dose information according to one representative embodiment.

FIG. 4 is a block diagram illustrating an example computer program product 300 for use in the automated system described above. The computer program product 300 can include a signal bearing medium 302, which can comprise a non-transitory computer readable medium 306, such as, but not limited to, a hard disk drive, a Compact Disc (CD), a Digital Video Disk (DVD), a digital tape, memory, etc. The computer program product 300 may also include a recordable medium 308, such as, but not limited to, memory, read/write (R/W) CDs, R/W DVDs, etc. In some implementations, the signal bearing medium 302 may encompass a communications medium 310, such as, but not limited to, a digital and/or an analog communication medium (e.g., a fiber optic cable, a waveguide, a wired communications link, a wireless communication link, etc.). Thus, for example, the computer program product 300 may be conveyed to one or more modules of the system 100 by a radio frequency (RF) signal bearing medium 302, where the signal bearing medium 302 is conveyed by a wireless communications medium 310 (e.g., a wireless communications medium conforming with the IEEE 802.11 standard). Instructions 304 are stored in the signal bearing medium 302 to direct the system to perform the image processing, automated dose extraction, and reporting as described above.

The computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by the sever 104. Any such computer storage media may be part of the server 104.

As noted above, the system may perform a dose adjustment based on patient size in operation 206. Manufacturers' dose reports are typically based on standard-sized acrylic phantoms, and do not reflect differences in patient size. For example, in the example dose screen illustrated in FIG. 1, a phantom diameter of 32 cm is assumed.

Figure 5:
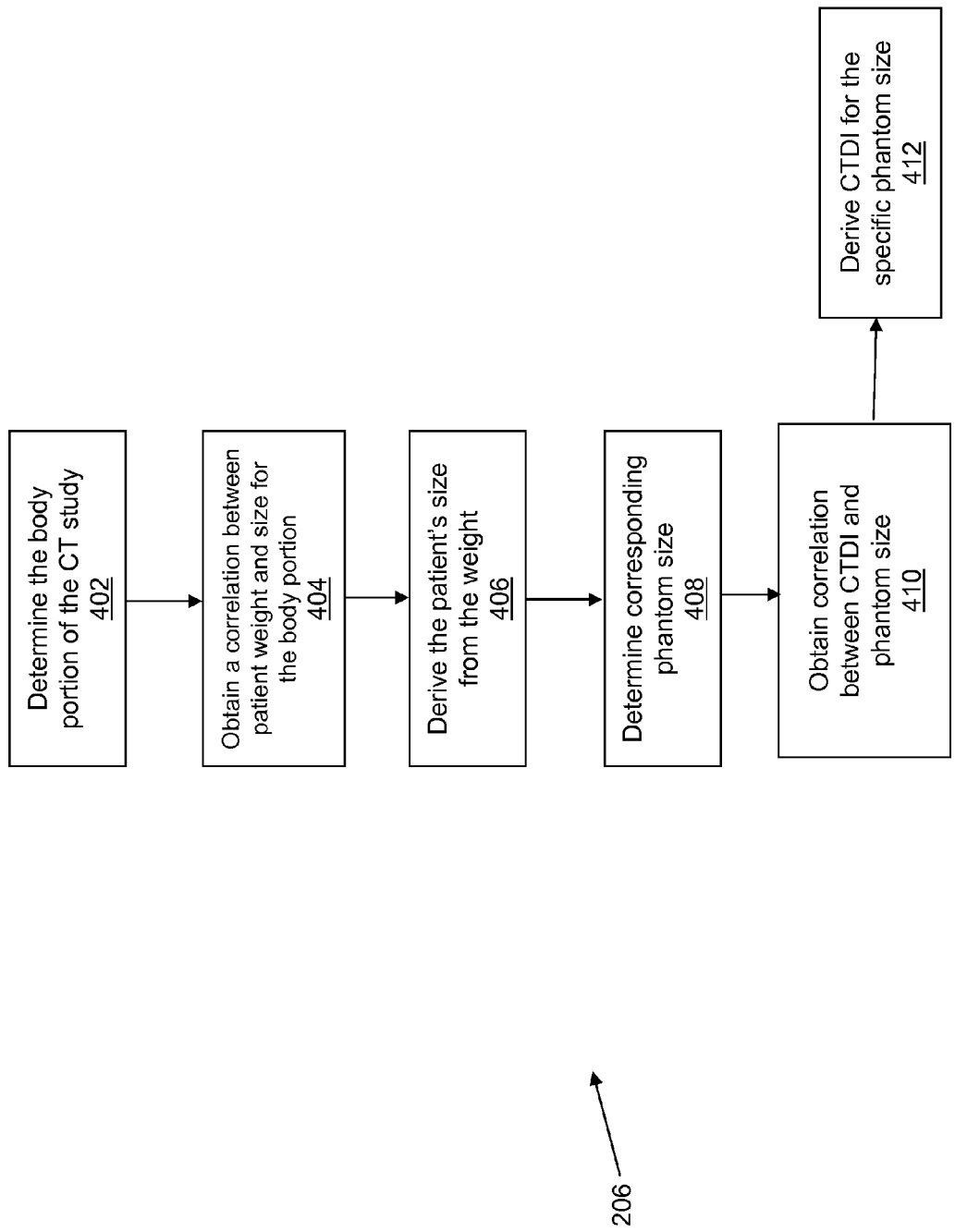
FIG. 5 is a flowchart illustrating an illustrative method for correcting a patient size.

As a result, the errors in these dose screens can be large, particularly when the patient size differs greatly from a standard sized patient. This can be especially true for pediatric patients for whom the reported doses may be erroneously low. In legacy CT studies, often the patients' sizes are not recorded in the dose screen, although the patients' weights are part of the record. To correct for the patients' sizes, in one embodiment, a correlation between patient weight and patient size is used to derive a patient's size. FIG. 5 is a flow diagram illustrating the operation 206 for correcting the patient's size in accordance with an illustrative embodiment.

In an operation 402, it is first determined which body portion is scanned in a CT study. For example, in FIG. 1, the "CT Description" indicates that the HALS/THORAX/ABDOMEN area was scanned. CT scans for other body parts, such as the head or the neck, may need size corrections different from those for the abdomen area.

Figure 6:
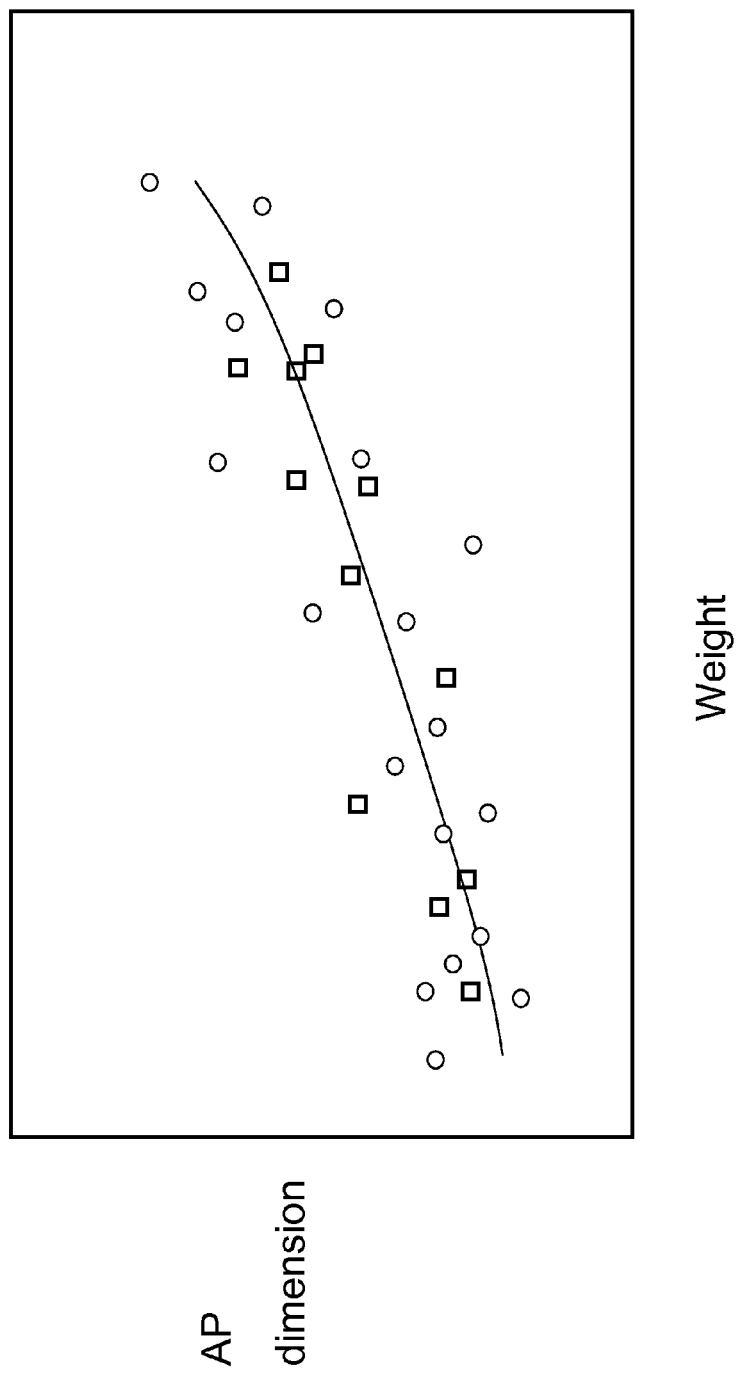
FIG. 6 is a plot illustrating an example correlation between patients' anteriorposterior dimensions and weights.

In an operation 404, a correlation between patient weight and size can be obtained for the specific body portion, e.g., the abdomen area. Such a correlation can be obtained from existing statistical studies. For example, with reference to FIG. 6, in a statistical study a large number of patients' abdomen anteroposterior dimension (AP, measured from front to back at the body section being scanned; in cm) were measured and plotted as a scattered plot against the measured patients' weights (W; in kg). A curve can be fit from the scattered plot. For example, in one study it was shown that a relationship of $$AP=111.4+1.376W+0.003573W^2 \quad (1)$$

fits the scattered plot satisfactorily.

Figure 7:
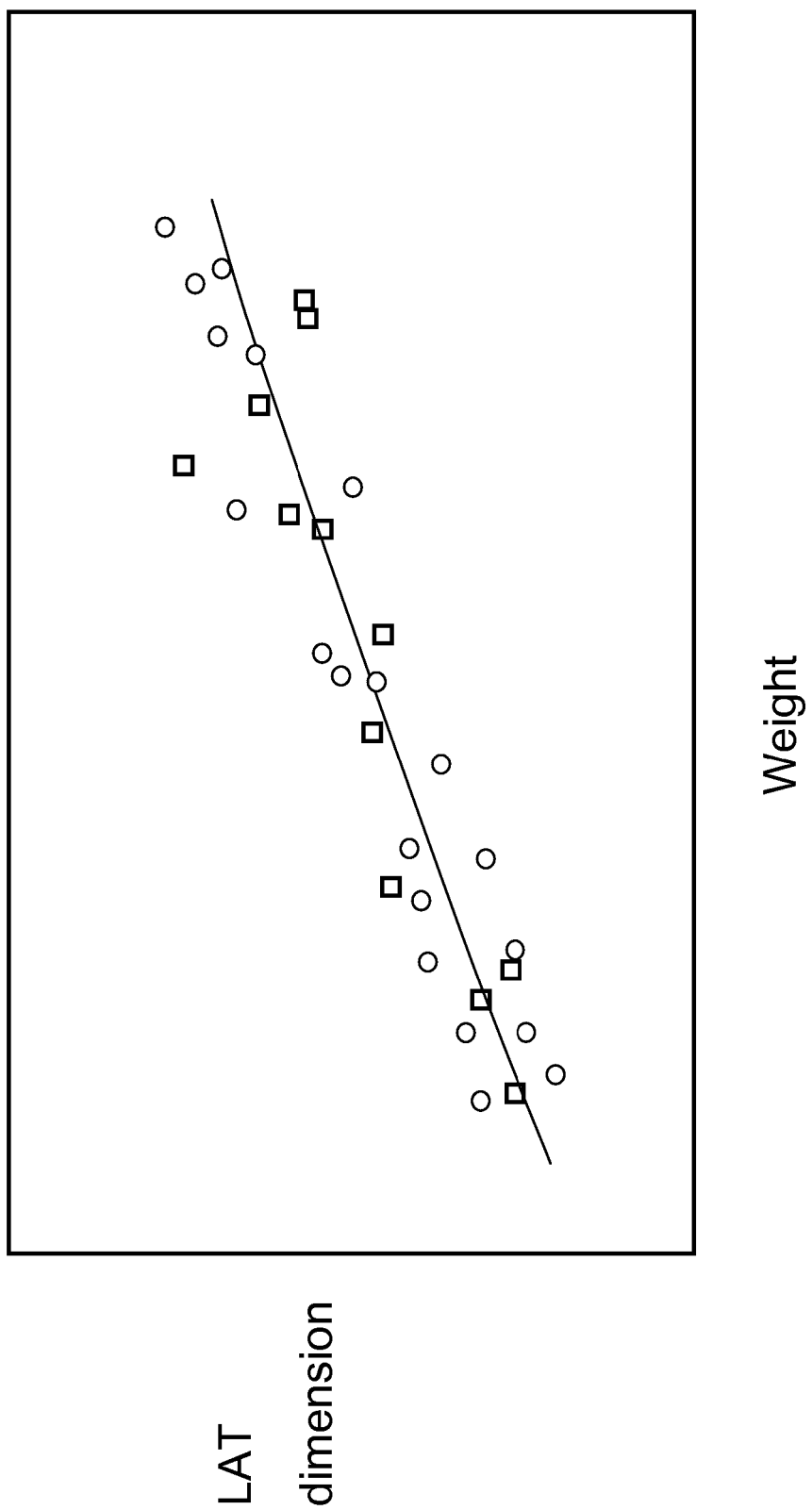
FIG. 7 is a plot illustrating an example correlation between patients' lateral dimensions and weights.

Similarly, referring to FIG. 7, in a statistical study a large number of patients' abdomen lateral dimension (LAT; in cm) were measured and plotted as a scattered plot against the measured patients' weights (W; in kg). A curve can also be fit from this scattered plot. For example, in one study it was shown that a relationship of $$LAT=143.7+2.710W+0.004319W^2 \quad (2)$$

fits the scattered plot satisfactorily.

As such, in an operation 406 of FIG. 5, the specific patient's size can be estimated using the above equations (1) and (2), from the patient's weight of record.

In an operation 408, an equivalent cylindrical phantom diameter corresponding to the estimated patient's weight can be determined using the following formula:

$$\text{Phantom diameter}=\text{square root}(AP*LAT)*C, \quad (3)$$

where C is the correction factor that takes into consideration the density difference between the soft tissue and the acrylic PMMA phantom material. Determination of the correction factor C is well known to those of skill in the art.

Figure 8:
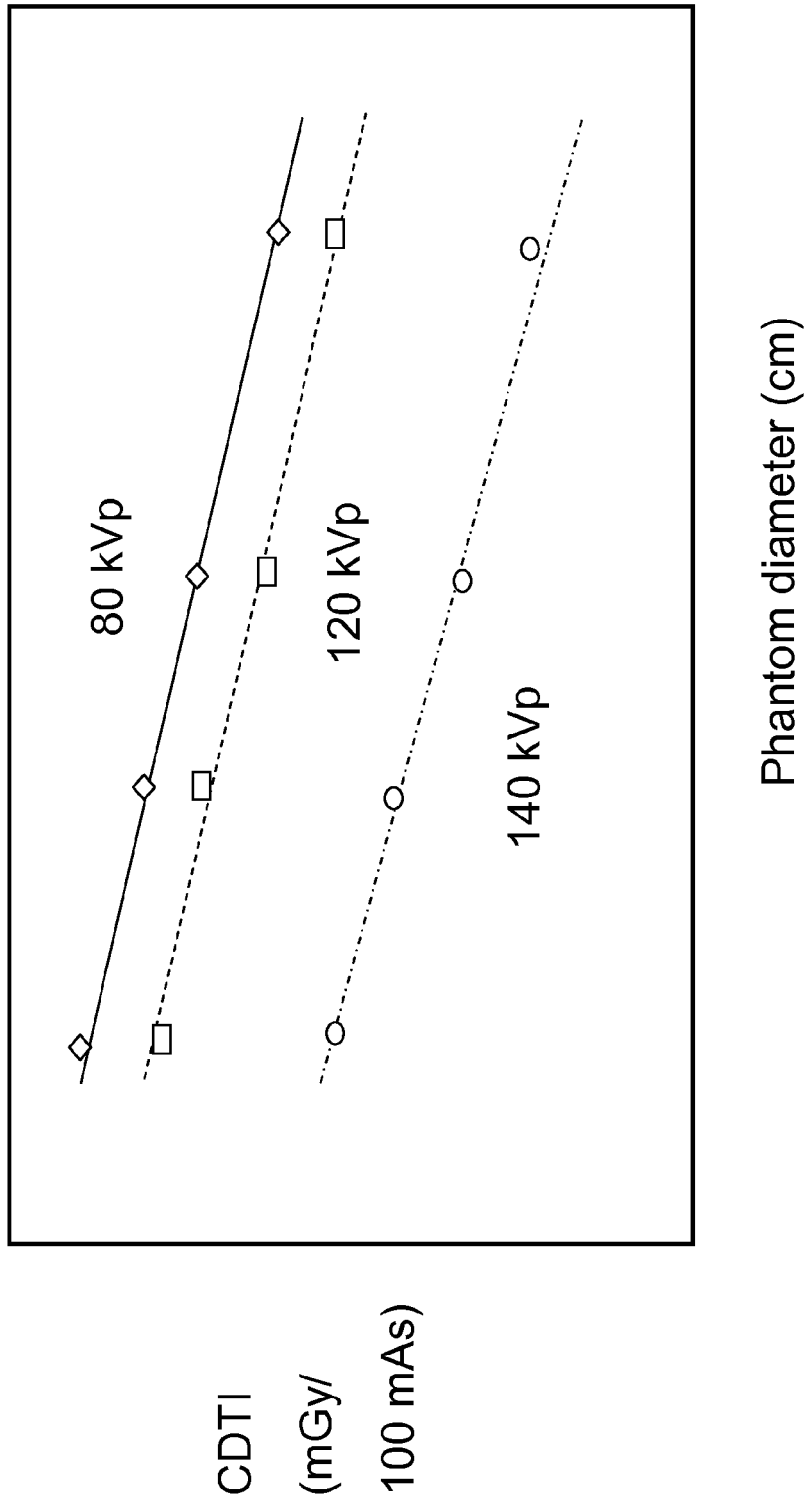
FIG. 8 is a plot illustrating an example correlation between radiation dose and phantom diameter.

Using the phantom diameter formula, corrections for the patient size can be made. Because the phantom size effect on the CTDI has been studied, a correction factor based upon the derived equivalent phantom size can be applied to the CTDI displayed in the dose screen shown in FIG. 1. In an operation 410, referring also to FIG. 8, for each CT scanner, and for a specific X-ray tube peak voltage, a relationship between CTDI (in units of mGy/100 mAs) can be measured for various phantom diameters. For a number of phantoms, a scattered plot of CTDI—phantom diameter is obtained, which generally shows an approximately linear relation. For each patient being scanned, in step 412 of FIG. 5, the CTDI corresponding to the corrected patient size is obtained from the correlation shown in FIG. 8.

Similar correction procedures can be used to obtain corrected CTDIvol and DLP, the latter being proportional to CTDIvol. In one embodiment, the DLP can be extracted as a primary dose descriptor because it includes both the CTDI and the scan length.

From the DLP, an effective dose can be estimated based upon conversion factors $W_T$. The conversion factor can be derived from Monte Carlo simulations, such as those published in European guidelines (EUR 16262 EN). In one example, the effective dose for an adult abdomen scan in mSv can be DLP*0.015, and the effective dose for an adult head scan in mSv can be DLP*0.0023. These different conversion factors can be obtained based on organ doses computed from Monte Carlo simulations and multiplied by tissue weighting factors, for example.

In an alternative embodiment, the patient size is measured and recorded, or can be derived from the CT images themselves. In one example, instead of estimating the patient size from patient weight information, the size correction can be done directly based upon the CT images. Because the CT number is linearly related to the linear attenuation coefficient of the material in the energy range of the CT scanning, the linear attenuation coefficient of the material is nearly proportional to the density of the material. The average CT number derived from a cross-sectional CT image is linearly correlated with the material mass. This relationship can be used to adjust the CTDI_vol and DLP for patient size and tissue composition.

In another example, a full Monte Carlo simulation can be performed for the interaction between the CT X-rays and a realistic numerical model of the patient's body derived from the CT images and/or magnetic resonance imaging (MRI) images. Effective dose can be readily obtained from the Monte Carlo simulation results, and the abovementioned patient size correction is not needed.

The embodiments disclosed herein can provide numerous benefits with respect to radiation safety awareness. For example, patient and/or public awareness can be promoted by keeping a log of radiation exposure in electronic medical records (EMR) and personal health records (PHR). Healthcare provider awareness can also be promoted through a feedback mechanism during electronic order entry. A notification or alert can be provided for recent diagnostic radiation exposures, to avoid redundant exams, or to suggest exams without radiation (e.g., MRI, ultrasound, etc.). The healthcare provider may be an institution, a hospital, a department, a physician's group, or individual healthcare professionals including radiologists and other specialists, physician's assistants, nurses, technical staff, or administrators. The automatic reporting system can be implemented within one institution or across multiple institutions, where the plurality of heterogeneous radiation-based medical imaging devices can be linked through a network. Radiation safety education of healthcare providers can also be improved by determining whether imaging practices are within national standards.

With the present system, longitudinal records of healthcare-related radiation exposure can be obtained. This is important to track radiation cumulatively over a patient's lifetime, and also has important implications for research involving the effects of healthcare-related, low-dose radiation exposure. Automated quality control (QC) of CT studies can be consistently performed to determine whether a particular study would cause the radiation dose outside the normal range. It is noted that the "normal" range can be different for different categories of studies. For example, a CT head scan would have a different expected radiation dose exposure compared with a CT chest scan.

In one embodiment, CT (or other) dose reports can be sent automatically after every CT exam is completed, and can be automatically processed by the system. The system receives CT dose reports from multiple CT scanners (or other devices) in a hospital. The processed radiation dose information is compared with a pre-defined dose threshold for the particular type of study (e.g., CT head, CT abdomen, CT chest, etc.). If the dose is above the threshold, an automated alert (e.g., an email, a short message, a voice message, or other types of notification) can be generated and sent, for example, to the physician or to a radiation safety team.

In one embodiment, archived dose reports may be automatically sent from the an archival or storage to the present system for processing of the dose information. The dose information can be compiled and sent to a downstream electronic medical record or a patient's personal health record (e.g., Google Health, Microsoft HealthVault, etc), to generate a lifetime record of medical radiation dose exposure for patients using the system disclosed herein.

In one embodiment, dose reports from both older scanners (which do not support radiation dose information in the DICOM metadata) and from new CT scanners (which support radiation dose in the DICOM metadata) are automatically sent to the system. The system can automatically extract radiation dose information from the dose reports or medical images obtained from the heterogeneous technologies. Dose information is processed and evaluated to determine if overexposure has occurred. A summary report can then be sent to downstream medical records or personal health records.

In one embodiment, dose reports can be automatically sent to the system for extracting radiation dose information. Periodic averages can be made for both individual patients and for individual ordering physicians. These averages can be compared with national averages to determine: (1) whether a particular patient has received significant healthcare-related radiation exposure as compared with a standard defined, e.g., through a study, by a professional association or a regulatory agency; or (2) whether an ordering physician has ordered more CT studies than others in the same specialty. A reporting threshold can be defined by the system provider, a hospital, a physicians' group or department, a study, a professional association, or a regulatory agency.

This information can be used to generate an alert to the radiation safety team or medical staff, for example, when it is determined that a patient is receiving too much radiation, or when one or more physicians may be ordering too many radiation-based studies compared with other physicians. The determination of too much radiation or too many radiation-based studies may be made based on the cumulative or average radiation received, or on cumulative or average studies ordered, or other statistical methods. The alert may be generated when a cumulative dose level or an average value is near, at, or above the relevant threshold. In the example, several alerts may be provided as percentages of proximity to the thresholds are met or exceeded. This dose information (either from the EMR or PHR) can be integrated with the order entry system, so that any medical staff ordering a new radiation-based study can see the history of the patient's radiation exposures, thereby reducing unnecessary or redundant exams.

As an example of the system in use, a random selection of 518 CT dose reports were processed by the system in accordance with one representative embodiment, and the dose information was extracted from the dose reports. The connected components algorithm was used in the dose extraction. The connected components arise from texts that have distinct characteristics, which can be reliably detected by established algorithms such as horizontal projection.

CT dose reports can be sent to the system using a standard DICOM "send" or other method to allow for an automated process to compile radiation dose and patient information in a web-based framework using a standard query language (SQL) or other database. Initial tests showed that the system accurately extracted dose information from 518 out of 518 (100%) CT dose reports. As such, the system provides a way to automatically track CT radiation dose on existing CT (or other) scanners, and does not rely on the DICOM SR Dose Report standard which is only available on the newest CT scanners.

WORKING EXAMPLE

In one example, the system according to one embodiment takes the image header of a CT dose screen 10 (shown in FIG. 1) as input, and identifies the fields 12 that are related to dose information, such as the CTDIvol, the DLP, and the total DLP, and the dose information shown in these fields are extracted. The patient information fields 14, including for example the patient name, the accession number, and the patient ID, can also be identified.

Although the foregoing refers to particular preferred embodiments, it will be understood that the disclosure is not so limited. It will occur to those of ordinary skill in the art that various modifications may be made to the disclosed embodiments and that such modifications are intended to be within the scope of the disclosure. All of the publications, patent applications and patents cited herein are incorporated herein by reference in their entirety.

What is claimed is:

1. A method comprising:
    automatically extracting radiation dose information for an individual patient from tomography images, wherein the tomography images includes at least one of text or symbols, wherein the radiation dose information is extracted from the at least one of text or symbols embedded in the tomography images;
    correcting the extracted radiation dose information using a formula specific to a body portion of the individual patient identified in the tomography images, wherein the body portion and the formula specific to the body portion are identified using the at least one of text or symbols embedded in the tomography images; and
    generating a report based on the corrected radiation dose information and the body portion of the individual patient identified in the tomography images, wherein the report is indicative of the individual patient's risk of radiation overexposure.

2. The method of claim 1, wherein the medical images comprise one of computed tomography (CT) or positron emission tomography-computed tomography (PET-CT) images.

3. The method of claim 1, wherein said automatically extracting dose information comprises performing an image segmentation on the medical images.

4. The method of claim 3, wherein performing the image segmentation comprises performing a connected component analysis.

5. The method of claim 4, wherein said connected component analysis is performed using DCMTK.

6. The method of claim 1, further comprising correcting the extracted radiation dose information for a size of the individual patient.

7. The method of claim 6, wherein correcting the extracted radiation dose information comprises obtaining a relationship between size of the individual patient and weight of the individual patient.

8. The method of claim 7, wherein correcting the extracted radiation dose information further comprises calculating an equivalent cylindrical phantom diameter based on the obtained relationship between the size of the individual patient and the weight of the individual patient.

9. The method of claim 8, wherein the equivalent cylindrical phantom diameter is calculated using:

phantom diameter=square root (*AP* dimension**LAT* dimension)**C*, wherein C is a correction factor that takes into consideration of the density difference between soft tissue and acrylic PMMA phantom material, AP dimension is the individual patient's anteriorposterior dimension, and LAT dimension is the individual patient's lateral dimension.

10. The method of claim 9, further comprising generating a respective correction factor for each of a plurality of heterogeneous CT scanners, wherein each respective correction factor is a function of patient weight.

11. The method of claim 6, further comprising determining a body portion of the individual patient that is scanned.

12. The method of claim 1, wherein said extracted radiation dose information comprises an effective dose.

13. The method of claim 1, further comprising storing the radiation dose information in a database.

14. The method of claim 1, further comprising storing the extracted radiation dose information in DICOM metadata of a medical image.

15. The method of claim 1, wherein extracting dose information comprises extracting dose information from medical images obtained from a plurality of heterogeneous CT scanners.

16. The method of claim 15, wherein at least one of the medical images obtained from the plurality of heterogeneous CT scanners includes no metadata indicative of exposure dose.

17. The method of claim 1, further comprising comparing the extracted radiation dose information with a predetermined threshold.

18. The method of claim 17, further comprising providing an alert if a radiation dose from the extracted radiation dose information is higher than the predetermined threshold.

19. The method of claim 1, further comprising displaying the report through a web interface.

20. The method of claim 1, wherein generating the report comprises generating an average dose for the individual patient.

21. The method of claim 20, further comprising providing an alert if a new CT study is ordered for the individual patient and the individual patient's risk of radiation overexposure exceeds a predetermined threshold.

22. The method of claim 1, wherein generating the report comprises generating a summary of a healthcare provider's history of ordering radiation-based studies.

23. The method of claim 1, further comprising sending the report through one of a short message, an email, a website, or a voice message.

24. A system comprising:
a computer configured to automatically extract radiation dose information for an individual patient from a tomography image, to correct the extracted radiation dose information using a formula specific to a body portion of the individual patient identified in the tomography image, wherein the body portion and the formula specific to the body portion are identified using the at least one of text or symbols embedded in the tomography image, and to generate a dose information report based on the corrected radiation dose information and the body portion of the individual patient identified in the tomography images, wherein the tomography image includes at least one of text or symbols, wherein the dose information report is indicative of the individual patient's risk of radiation overexposure, and wherein the radiation dose information is extracted from the at least one of text or symbols embedded in the tomography image.

25. The system of claim 24, wherein at least some of the radiation dose information is extracted from image data not in DICOM format.

26. The system of claim 25, wherein the medical image comprises one of computed tomography (CT) or positron emission tomography-computed tomography (PET-CT) images.

27. The system of claim 25, further comprising a communication device configured to transmit the dose information report to a requesting device.

28. The system of claim 25, further comprising at least one of a picture archiving and communication system (PACS) or a radiology information system (RIS).

29. A non-transitory computer readable medium containing instructions therein, wherein the instructions comprise:
automatically extracting radiation dose information for an individual patient from a medical image, wherein the medical image includes at least one of text or symbols, wherein the radiation dose information is extracted from the at least one of text or symbols embedded in the medical image;
correcting the extracted radiation dose information using a formula specific to a body portion of the individual patient identified in the tomography images, wherein the body portion and the formula specific to the body portion are identified using the at least one of text or symbols embedded in the tomography images; and
generating a dose information report indicative of the individual patient's risk of radiation overexposure.

30. The non-transitory computer readable medium of claim 29, wherein the medical image comprises one of computed tomography (CT) or positron emission tomography-computed tomography (PET-CT) images.

31. The non-transitory computer readable medium of claim 29, wherein said automatically extracting dose information comprises performing an image segmentation on the medical image.

32. The non-transitory computer readable medium of claim 31, wherein performing the image segmentation comprises performing a connected component analysis.

33. The non-transitory computer readable medium of claim 32, wherein said connected component analysis is performed using DCMTK.

34. The non-transitory computer readable medium of claim 29, wherein the instructions further comprise correcting the extracted radiation dose information for a size of the individual patient.

35. The non-transitory computer readable medium of claim 34, wherein correcting the extracted radiation dose information comprises obtaining a relationship between size of the individual patient and weight of the individual patient.

36. The non-transitory computer readable medium of claim 35, wherein correcting the extracted radiation dose information further comprises calculating an equivalent cylindrical phantom diameter based on the obtained relationship between the size of the individual patient and the weight of the individual patient.

37. The non-transitory computer readable medium of claim 36, wherein the equivalent cylindrical phantom diameter is calculated using:

phantom diameter=square root(*AP* dimension**LAT* dimension)**C*, wherein C is a correction factor that takes into consideration of the density difference in soft tissue and in acrylic PMMA phantom material, AP dimension is the individual patient's anteriorposterior dimension, and LAT dimension is the individual patient's lateral dimension.

38. The non-transitory computer readable medium of claim 37, wherein the instructions further comprise generating a correction factor as a function of patient weight for a CT scanner.

39. The non-transitory computer readable medium of claim 29, wherein the instructions further comprise storing the radiation dose information in a database.

40. The non-transitory computer readable medium of claim 29, wherein the instructions further comprise storing the radiation dose information in DICOM metadata of a medical image.

41. The non-transitory computer readable medium of claim 29, wherein extracting dose information comprises extracting dose information from a plurality of heterogeneous CT scanners.

42. The non-transitory computer readable medium of claim 41, wherein at least some of the radiation dose information extracted from at least some of the plurality of heterogeneous CT scanners are not in DICOM format.

43. The non-transitory computer readable medium of claim 29, wherein the instructions further comprise comparing the extracted radiation dose information with a predetermined threshold.

44. The non-transitory computer readable medium of claim 43, wherein the instructions further comprise providing an alert if a radiation dose from the extracted radiation dose information is higher than the predetermined threshold.

45. The non-transitory computer readable medium of claim 29, wherein the instructions further comprise displaying the dose information report through a web interface.

46. The non-transitory computer readable medium of claim 29, wherein said generating a report comprises generating an accumulative or an average radiation dose information for a patient.

47. The non-transitory computer readable medium of claim 29, wherein the instructions further comprise providing an alert if a new CT study is ordered for the individual patient and the individual patient's risk of radiation overexposure exceeds a predetermined threshold.

48. The non-transitory computer readable medium of claim 29, wherein said generating a report comprises generating a summary of a healthcare provider's history of ordering radiation-based studies.

49. The non-transitory computer readable medium of claim 29, wherein the instructions further comprise sending the report through one of a short message, an email, a website, or a voice message.

* * * * *